(12) United States Patent
Lee et al.

(10) Patent No.: US 10,478,479 B2
(45) Date of Patent: Nov. 19, 2019

(54) METHOD FOR PREPARING DENDRITIC CELL, DENDRITIC CELL PREPARED THEREBY, AND USE THEREOF

(71) Applicant: JW CREAGENE INC., Gyeonggi-do (KR)

(72) Inventors: Yoon Lee, Gyeonggi-do (KR); Young-Mok Kim, Seoul (KR); So-Yeon Kim, Gyeonggi-do (KR); Seung-Soo Han, Gyeonggi-do (KR); Yong-Soo Bae, Gyeonggi-do (KR)

(73) Assignee: JW CREAGENE INC., Gyeonggi-Do (KR)

( * ) Notice: Subject to any disclaimer, the term of this patent is extended or adjusted under 35 U.S.C. 154(b) by 137 days.

(21) Appl. No.: 15/327,933

(22) PCT Filed: Jul. 28, 2015

(86) PCT No.: PCT/KR2015/007892
§ 371 (c)(1),
(2) Date: Jan. 20, 2017

(87) PCT Pub. No.: WO2016/018053
PCT Pub. Date: Feb. 4, 2016

(65) Prior Publication Data
US 2017/0196955 A1 Jul. 13, 2017

(30) Foreign Application Priority Data

Aug. 1, 2014 (KR) ........................ 10-2014-0099281

(51) Int. Cl.
*A61K 35/12* (2015.01)
*A61K 39/00* (2006.01)
*C12N 5/0784* (2010.01)

(52) U.S. Cl.
CPC .......... *A61K 39/0011* (2013.01); *A61K 35/12* (2013.01); *C12N 5/0639* (2013.01); *A61K 2039/5154* (2013.01); *C12N 2501/02* (2013.01); *C12N 2501/2301* (2013.01); *C12N 2501/2306* (2013.01); *C12N 2501/24* (2013.01); *C12N 2501/25* (2013.01); *C12N 2501/727* (2013.01); *C12N 2501/999* (2013.01)

(58) Field of Classification Search
CPC ... A61K 39/0011; A61K 35/12; C12N 5/0639
USPC ...................................................... 424/277.1
See application file for complete search history.

(56) References Cited

U.S. PATENT DOCUMENTS

| | | |
|---|---|---|
| 2005/0003533 A1 | 1/2005 | Kalinski |
| 2009/0029387 A1 | 1/2009 | Jung et al. |
| 2013/0195919 A1 | 8/2013 | Von Andrian et al. |
| 2014/0037606 A1 | 2/2014 | Amiel |

FOREIGN PATENT DOCUMENTS

| | | | |
|---|---|---|---|
| CN | 101680016 A | 3/2010 | |
| CN | 102439137 A | 5/2012 | |
| EP | 1209226 A2 | 5/2002 | |
| JP | 2006-502703 A | 1/2006 | |
| JP | 2010-527234 A | 8/2010 | |
| JP | 2019-527234 A | 8/2010 | |
| JP | 2011-515110 A | 5/2011 | |
| JP | 2013-521002 A | 6/2013 | |
| KR | 10-2006-0122623 A | 11/2006 | |
| KR | 20060122623 | * 11/2006 | |
| KR | 10-2008-0101988 A | 11/2008 | |
| KR | 10-2010-0089151 A | 8/2010 | |
| KR | 1020100089151 | * 8/2010 | ........... C07K 14/705 |
| WO | 03000907 A2 | 1/2003 | |
| WO | 2006126865 A1 | 11/2006 | |
| WO | 2006127150 A2 | 11/2006 | |
| WO | WO2013180481 A1 | 12/2013 | |

OTHER PUBLICATIONS

Amiel, E., et al., "Inhibition of mTOR promotes dendritic cell activation and enhances therapeutic autologous vaccination in mice1", "The Journal of Immunology", Sep. 1, 2012, pp. 2151-2158, vol. 189, No. 5, Publisher: NIH Public Access.

Fujimasa, T., et al, "Phase I/II study of immunotherapy using tumor antigen-pulsed dendritic cells in patients with hepatocellular carcinoma", "International Journal of Oncology", Nov. 11, 2012, pp. 1601-1609, vol. 41, No. 5.

Reinhard, G., et al., "Generation of dendritic cell-based vaccines for cancer therapy", "British Journal of Cancer", Jan. 1, 2002, pp. 1529-1533, Publisher: www.bjcancer.com.

Yang, A., et al., "Molecular Characterization of Antigen-Peptide Pulsed Dendritic Cells: Immature Dendritic Cells Develop a Distinct Molecular Profile when Pulsed with Antigen Peptide", "PLOS ONE", Jan. 27, 2014, pp. e86306, vol. 9, No. 1, Publisher: www.plosone.org.

Eagle, H., "Amino Acid Metabolism in Mammalian Cell Cultures", "Science", Aug. 21, 1959, pp. 432-437, vol. 130.

Hsu, F.J., et al., "Vaccination of Patients with B-Cell Lymphoma Using Autologous Antigen-Pulsed Dendritic Cells", "Nature Medicine", Jan. 1996, pp. 52-58, vol. 2, No. 1.

Inaba, K., et al., "Dendritic Cells as Antigen Presenting Cells in Vivo", "International Reviews of Immunology", 1990, pp. 197-206, vol. 6.

(Continued)

*Primary Examiner* — Yan Xiao
(74) *Attorney, Agent, or Firm* — Hultquist, PLLC; Steven J. Hultquist

(57) ABSTRACT

The present invention relates to a method for preparing a dendritic cell, a dendritic cell prepared thereby and a use thereof, and more specifically, to a method for preparing a dendritic cell, including: treating a dendritic cell at a maturation stage rather than at an immature stage with an antigen bound to a peptide having a cell membrane permeability to prepare a dendritic cell with improved antigen-presenting ability, a dendritic cell prepared by the method, and an immunotherapeutic agent thereof, a use for anti-tumor vaccines, or a pharmaceutical composition for treating tumors, containing the same.

3 Claims, 10 Drawing Sheets

Specification includes a Sequence Listing.

(56) References Cited

OTHER PUBLICATIONS

Inaba, K., et al., "Dendritic Cell Progenitors Phagocytose Particulates, Including Bacillus Calmette-Guerin Organisms, and Sensitize Mice to Mycobacterial Antigens In Vivo", "Journal of Experimental Medicine", Aug. 1993, pp. 479-488, vol. 178, Publisher: The Rockefeller University Press.

Kim, D., et al., "Cytoplasmic Transduction Peptide (CTP): New Approach for the Delivery of Biomolecules into Cytoplasm in vitro and in vivo", "Experimental Cell Research", Feb. 7, 2006, pp. 1277-1288, vol. 312.

Note: For the non-patent literature citations that no month of publication is indicated, the year of publication is more than 1 year prior to the effective filing date of the present application.

* cited by examiner

METHOD FOR PREPARING DENDRITIC CELL, DENDRITIC CELL PREPARED THEREBY, AND USE THEREOF

CROSS-REFERENCE TO RELATED APPLICATIONS

This application is a U.S. national phase under the provisions of 35 U.S.C. § 371 of International Patent Application No. PCT/KR15/07892 filed Jul. 28, 2015, which in turn claims priority of Korean Patent Application No. 10-2014-0099281 filed Aug. 1, 2014. The disclosures of such international patent application and Korean priority patent application are hereby incorporated herein by reference in their respective entireties, for all purposes.

TECHNICAL FIELD

The present invention relates to a method for preparing a dendritic cell, a dendritic cell prepared thereby and a use thereof, and more specifically, to a method for preparing a dendritic cell, including: treating a dendritic cell at a maturation stage rather than at an immature stage with an antigen bound to a peptide having a cell membrane permeability to prepare a dendritic cell with improved antigen-presenting ability, a dendritic cell prepared by the method, and an immunotherapeutic agent thereof, a use for anti-tumor vaccines, or a pharmaceutical composition for treating tumors, containing the same.

BACKGROUND ART

Dendritic cells are professional antigen presenting cells (APCs), and play an important role in immune induction and immune regulation in a body.

The dendritic cells in a human body are only 0.3% of total white blood cells, but are immune cells capable of activating naive T cells that have never contacted antigens to induce a primary immune response, and to induce an antigen-specific acquired memory immune. The reason in which the dendritic cells are able to serve as the professional antigen presenting cells is that co-stimulatory molecules such as CD80 and CD86 and adhesion molecules such as ICAM-1 in addition to major histocompatibility complex (MHC) I/II are highly expressed on a cell surface, and various cytokines (interferon, IL-12, IL-18, etc.) related to T cell activation are secreted in a large amount.

As described above, since the dendritic cells are able to effectively induce or regulate antigen-specific T cell activity, a possibility in which the dendritic cells are used as a therapeutic agent for cancer or intractable immune diseases has been studied for a long time. It was found that when the dendritic cells directly separated from tissue or blood or dendritic cells differentiated from monocytes are sensitized with an antigen and matured dendritic cells are injected back into the body, it induces a professional antigen-specific cytotoxic T lymphocyte (CTL), and thus, a possibility of developing the dendritic cells as a vaccine for treatment of cancer or infectious diseases has been studied for a long time (Inaba, K. et al., 3. Exp. Med., 178:479, 1993; Inaba, K. et al., Int. Rev. Immunol., 6:197, 1990; Hsu, F. et al., Nature Med., 2:52, 1996).

Based on these early study results, clinical studies of dendritic cell therapy for cancer treatment have been actively conducted all over the world, and results have been reported in various carcinomas. However, clinical effects with a single therapy are less than the initial expectation.

The known reason why the dendritic cell therapy has not been successful yet is due to low immunogenicity of tumor cells and immunosuppressive substances secreted by cancer cells. In this case, if the dendritic cells are able to induce more professional anti-cancer immunity to overcome low immunogenicity of tumor cells and to induce anti-cancer immunity that is able to surpass an immunosuppressive ability of the tumor cells, therapeutic effects may be greatly improved. Under these circumstances, present inventors found that when the dendritic cells at a maturation stage rather than an immature stage were sensitized with a recombinant antigen in which an antigen is bonded with a functional peptide having a cell membrane permeability such as cytoplasmic transduction peptide [CTP: Kim, D. et al. Exp Cell Res. 312(8):1277-88, 2006], it was possible to prepare dendritic cells having remarkably improved lymph node migration ability, T cell proliferation ability, cytotoxic T lymphocyte induction ability, etc., than those of conventional dendritic cells, and confirmed that it was possible to provide an immunotherapeutic agent thereof using the same, and a pharmaceutical composition for preventing or treating tumors using the same, and completed the present invention.

DISCLOSURE

Technical Problem

An object of the present invention is to provide a method for preparing a dendritic cell having improved cytotoxic T lymphocyte induction ability and improved function, a dendritic cell prepared by the method, and an anti-tumor vaccine or a pharmaceutical composition for treating tumors containing the same.

Technical Solution

In order to achieve the foregoing objects, the present invention provides a method for preparing a dendritic cell comprising sensitizing a dendritic cell, which is treated and cultured with a maturation factor, with an antigen bound to a peptide having cell permeability.

The present invention also provides a dendritic cell prepared by the method.

The present invention also provides an immunotherapeutic agent containing the dendritic cell.

The present invention also provides an anti-tumor vaccine containing the dendritic cell.

The present invention also provides a pharmaceutical composition for treating tumors containing the dendritic cell.

DESCRIPTION OF DRAWINGS

FIG. 1A shows migration ability of a dendritic cell prepared in an exemplary embodiment of the present invention by treating a peptide having cell-permeability with an immature dendritic cell from an immature stage to O/N (20 hours), and by treating the same antigen at 4 hours before cell harvest during a maturation process.

FIG. 1B shows analysis results of IL-12 concentration in a dendritic cell culture medium of FIG. 1A.

FIG. 1C shows analysis results of T cell proliferation ability when the dendritic cells of FIG. 1A and autologous T cells are co-cultured.

FIG. 1D shows ELISA analysis results of IFN-γ in the culture medium of FIG. 1C.

FIG. 2A shows analysis results of the number of cytotoxic T lymphocytes (CTL) induced with dendritic cells prepared at different antigen sensitization times according to an exemplary embodiment of the present invention.

FIG. 2B shows analysis result of concentration of IFN-γ secreted in a culture medium during the induction of cytotoxic T lymphocytes (CTL) according to an Example (FIG. 2A).

FIG. 2C shows results of examining a cytotoxic activity of the CTL (effector cell) prepared in Example (FIG. 2A).

FIG. 2D shows analysis results of concentration of IFN-γ secreted in the culture media when the CTL (effector cell) of Example (FIG. 2C) and target cells are co-cultured.

FIG. 2E shows analysis results of antigen-specificity of the CTL induced in the Example (FIG. 2A), using IFN-γ ELISPOT assay.

FIG. 4A shows phenotypic analysis results of dendritic cells sensitized with the antigen combined with or without CTP (cytoplasmic transduction peptide) at O/N (20 hours) or at 4 hours before cell harvest.

FIG. 4B shows ELISA analysis results of IFN-γ in a culture medium when the dendritic cell of Example (FIG. 4A) and an autologous T cell were co-cultured.

FIG. 4C shows analysis results of CD8 positive cells of induced CTL by the dendritic cell of Example (FIG. 4A).

FIG. 4D shows ELISA analysis results of IFN-γ in a supernatant during a process of inducing the CLT with the dendritic cell of Example (FIG. 4A).

FIG. 4E shows analysis results of antigen-specific immune response of T cells induced by the dendritic cell of Example (FIG. 4A), using IFN-γ ELISPOT.

FIG. 4F shows test results obtained by examining CD8 positive cells expressing granule (Granzyme B) among T cells induced by the dendritic cell of Example (FIG. 4A), using an intracellular staining method.

FIG. 6A shows a diagram of a CTP-GPC3 treatment method, and FIG. 6B shows analysis results of IFN-γ in the culture media when respective dendritic cells and autologous T cell are co-cultured, using an ELISA method.

BEST MODE

Figure 1A:
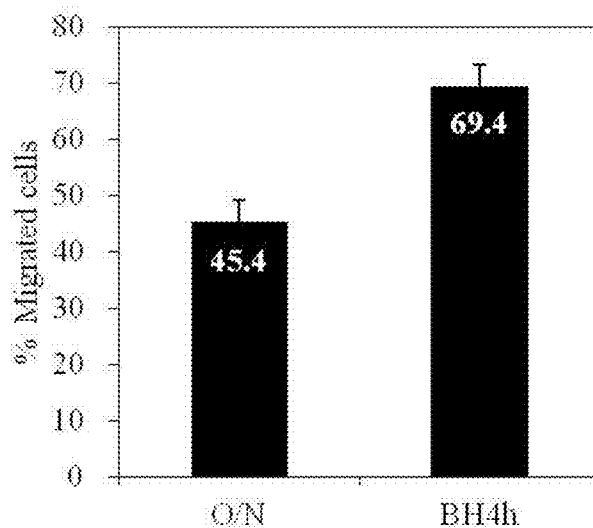
FIGS. 1A to 1D show results as follows.

Unless defined otherwise, all the technical and scientific terms used herein have the same meanings as those generally understood by persons skilled in the art to which the present invention pertains. Generally, the nomenclature used herein are well known and commonly employed in the art.

An antigen uptake ability of mature dendritic cells is much lower than that of immature cells in a conventional method for preparing dendritic cells, such that a method for delivering an antigen before maturation of the dendritic cells is utilized (Korean Patent Application Publication No. 2004-0025690). In addition, types of the antigen to be delivered are mRNA, DNA, lysate of cancer cells or tissues, cancer cells which are killed or apoptosis-induced, recombinant proteins and short peptides, and these antigens are directly treated on the dendritic cells or these antigens are delivered to the dendritic cells using methods such as co-culturing with the dendritic cells, electroporation, lipofectamine, etc. In particular, according to the electroporation, transfection efficiency varies greatly depending on the delivered cells, and even though high cell viability is shown after 24 hours of culturing by electroporation, it is shown that cell recovery ratio is low. A method for delivering an antigen using lipid vesicles such as liposomes also shows low transfection efficiency, physico-chemical instability, low emulsion stability and collection efficiency, and requires a process for removing solvents, and thus, there are a number of problems in that a manufacturing process is complicated, and the manufacturing cost is increased, etc.

According to the present invention, a recombinant antigen bound to a peptide having a cell membrane permeability is simply treated in a culture medium during the culturing of dendritic cells by treating a maturation factor, such that the antigen passes through a cell membrane and remains in cytoplasm without an antigen-capturing ability of the dendritic cell, and the peptide prepared by proteasome is loaded on MHC I, and thus, it is possible to very effectively induce an activity of cytotoxic T lymphocyte (CTL) when administered in a body. Further, full-length proteins are usable, which has no HLA limitation unlike the peptide, and thus, the preparation method according to the present invention may be widely utilized in preparing a dendritic cell therapeutic agent. In view of function, it is possible to induce immunity against various CTL epitopes of the full-length protein as compared to dendritic cells prepared using conventional short CTL peptides, and thus, a strong therapeutic effect may be expected.

The present inventors found that when the dendritic cells are sensitized using an antigen bound to a cell membrane penetrating peptide after immature dendritic cells are—maturated in the presence of the maturation factor, unlike the conventional method in which the immature dendritic cells are sensitized with the antigen first and then matured with maturation factors, a migration ability is improved, IL-12 secretion ability when the dendritic cells are re-stimulated is improved, T cell proliferation ability in co-culturing with T cells is improved, Th1 reactivity is improved, and cytotoxic T lymphocyte induction ability is improved, etc., as compared to the conventional dendritic cells obtained by treating the immature dendritic cells with the antigen.

According to these results, it is considered that the mature dendritic cells immediately decompose and present the antigen introduced into the cells without an antigen-capturing process, such that the loss of the peptide in a MHC-peptide binding state is reduced, and the cells are directly delivered to the T-cell, resulting in strong induction of an antigen-specific reaction. Term "dendritic cell" as used herein refers to a professional antigen presenting cell that absorbs an antigen into a cell, and treats the cell to present the antigen or a peptide derived from the antigen, together with an MHC class I complex or MHC class II complex. The dendritic cell includes both immunogenic and tolerogenic antigen presenting cells, and is classified into an immature dendritic cell ("imDC") and a mature dendritic cell (or matured dendritic cell: "mDC") depending on maturity.

Term "immature dendritic cell" used herein refers to a dendritic cell that is found at an early stage of maturation, and does not express cell surface markers such as CD14 similar to the mature dendritic cell, and expresses HLA-DR, CD86, CD80, CD83 or CD40 at a low level, and expresses CD1a and CCR1, CCR2, CCR5 and CXCR1 at normal level.

The level of such surface trait markers is able to be confirmed through Examples of the present invention. It was confirmed under conditions of the Examples according to the present invention that expression of CD80 and CD83 had a level of about 20% or less in the immature dendritic cell, and in particular, expression of CD83 which is a representative maturation marker was less than 10%. Differentiation of the immature dendritic cell is initiated by receiving a variety of signals, which leads to complete differentiation or partial differentiation depending on combination of signals to be received. The immature dendritic cell is not able to activate the T cell even in contact with the T cell due to a low level of inflammatory cytokine that is expressed.

Term "mature dendritic cell" used herein refers to a cell formed by maturation of the immature dendritic cell, and means a cell in which cell surface markers involved in B and T cell activity, for example, MHC class I or MHC class II (HLA-DR), cell attachment factors (CD54, CD18, CD11), co-stimulatory factors (for example, CD86, CD80, CD83 or CD40) are expressed at a high or relatively increased level as compared to the immature dendritic cell. Typically, the mature dendritic cell expresses CCR7 and CXCR4 at high levels. For example, when the immature dendritic cell is cultured in the presence of the maturation factors to induce the maturation of the dendritic cell in an exemplary embodiment of the present invention, it could be confirmed that expression ratios of CD83 and CD80 were remarkably increased. In addition, the mature dendritic cell releases proinflammatory cytokines, and increases proliferation of allogeneic T cells and syngeneic T cells and/or increases secretion for expression of cytokines related to other immune responses in a mixed lymphocyte reaction.

In the preparation method of the present invention, the dendritic cell is sensitized with the antigen in a form of a recombinant antigen bound to a cell membrane penetrating peptide, wherein sensitization time may be, for example, 24 hours or less, to sensitize the dendritic cell according to the present invention, preferably, 12 hours or less, and more preferably 8 hours or less, to sensitize the dendritic cell according to the present invention. The sensitization time of the antigen may be controlled by the types of antigen and a maturation degree of immature dendritic cell. A minimum sensitization time of the antigen is preferably, for example, 1 hour or more, or 3 hours or more. However, the minimum sensitization time may also be controlled by a method for culturing antigen-sensitized dendritic cells, such as antigen size, species, and the number of sensitized cells.

A time point at which the antigen is treated is not particularly limited as long as it is in a process in which the immature dendritic cell is cultured and matured, or before the mature dendritic cells are collected or harvested after the maturation is completed, but for example, may be within 1 to 48 hours, 2 to 48 hours, 6 to 48 hours, 12 to 48 hours, 1 to 40 hours, 2 to 40 hours, 6 to 40 hours, 1 hour to 24 hours, 2 to 24 hours, 6 to 24 hours, or 12 to 24 hours after the maturation factor is treated.

When the antigen is treated after the maturation within the above-described time range, it is possible to obtain an effect of enhancing antigen-specific Th1 immunity and CTL induction ability. However, when the time point at which the antigen is treated is beyond the above-described time range, there may be a problem that functions of the dendritic cell are exhausted beyond the maturation stage.

Figure 3:
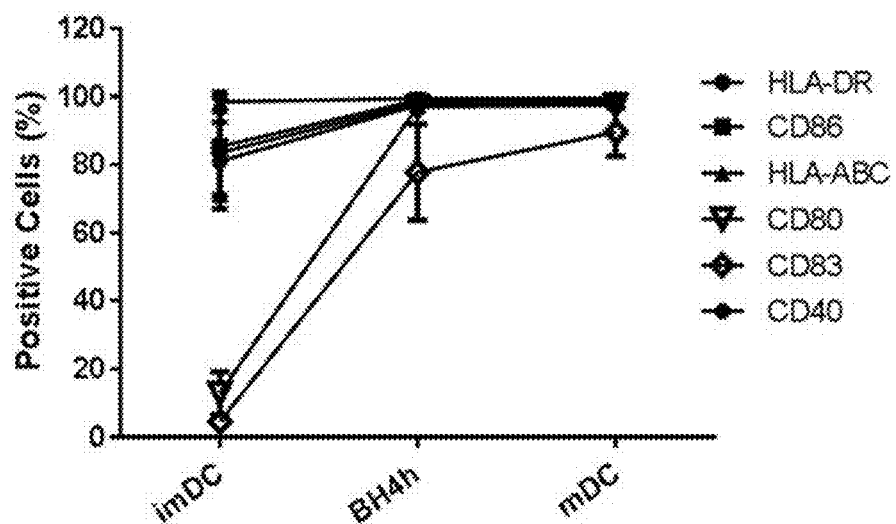
FIG. 3 shows phenotypic analysis results of dendritic cells prepared according to an exemplary embodiment of the present invention.

Further, culturing time for inducing the maturation of the immature cell as described above may be varied depending on the culture conditions, and the time point at which the antigen is treated may be determined based on the cell surface marker such as CD80, CD83, or CD40 of which an expression amount increases during the maturation of the dendritic cell. For example, the dendritic cell may show an increased expression level of CD80, CD83, and CD40 by about 50% or more, and preferably about 60% or more increased as compared to that of the immature dendritic cell (FIG. 3). If it is possible to achieve a maturation level, the culturing time is not limited with the above-mentioned conditions.

In one example, the peptide having a cell membrane permeability may be at least one protein transport domain selected from the group consisting of CTP (cytoplasmic transduction peptide), HP4, Hph-1, Mph-1, Sim-2, Tat, VP22, Antp (Antennapedia), Pep-1 (peptide), PTD-5, R9 (arginine), and peptide including 7R domain. Accordingly, by binding the peptide remaining in cytoplasm while having the excellent cell membrane permeability to the antigen, it is possible to prepare a professional dendritic cell vaccine having improved cytotoxic T lymphocyte induction ability.

Among the above peptides, the cytoplasmic transduction peptide exhibits a cell membrane permeation phenomenon even after treatment with proteolytic enzymes (for example, trypsin, chymotrypsin and subtilisin) after a suitable time required for cell membrane permeation has elapsed, such that the peptide is able to penetrate through cell membranes without being affected by the treatment of the proteolytic enzymes.

For example, the cytoplasmic transduction peptide may be a peptide including an amino acid sequence selected from the group consisting of SEQ ID NOs: 1 to 14, preferably, a peptide including an amino acid sequence selected from the group consisting of SEQ ID NOs: 1 to 6, 8 to 10 and 13 to 14, and more preferably, a peptide including an amino acid sequence selected from the group consisting of SEQ ID NOs: 1 to 2 and 13 to 14.

The binding of the peptide to the antigen may be achieved as long as it is an intermolecular binding type known in the art, but for example, the peptide is bound to the antigen via a covalent bond of the peptide and the antigen, or a conjugation form of the peptide and the antigen using a specific linker.

The antigen covalently bound to the cytoplasmic transduction peptide may be bound to an N-terminal or a C-terminus of the cytoplasmic transduction peptide. The covalent bond method may be performed by a method known in the art depending on the kinds of antigen. For example, it is performed by cloning a gene encoding cytoplasmic transduction peptide-protein and expressing the gene in a cell. In addition, a linker that does not interfere with transportability of the cytoplasmic transduction peptide and cytoplasmic persistence and an activity of biologically active molecules may be used. The linker may be, for example, N-succinimidyl iodoacetate, N-maleimidobutyryloxysuccinamide ester, 1,5-difluoro-2,4-dinitrobenzene, disdiazobenzidine, 3,3-dithio-bis-(sulfosuccinimidyl-propionate), ethylene glycol bis (sulfosuccinimidyl succinate), dicyclohexyl carbodiimide, etc., but is not limited thereto. On the other hand, when the activity is exhibited only when the antigen is decomposed from the cytoplasmic transduction peptide, the linker that is able to be cleaved in vivo is used. For example, a binding agent having carboxylic acid ester and/or having a disulfide bond may be used.

When the mature dendritic cell is treated with the antigen to which the cell membrane penetrating peptide, for example, the cytoplasmic transduction peptide is bound, it could be confirmed that permeability into cells is remarkably improved, the uptake efficiency of the antigen is increased, and the migration ability of the dendritic cell, production of IL-12, T-cell proliferation, and production of IFN-γ are remarkably increased as compared to a control group to which the cell membrane penetrating peptide is not bound. These results are opposite to conventional results that antigen sensitization to the dendritic cell should be be performed prior to maturation, which were firstly demonstrated by the present invention.

The maturation factors that are treated during the culture for maturation of the immature dendritic cell may be, for example, at least one selected from the group consisting of Interleukin-1β (IL-1β), Interleukin-6 (IL-6), Tumor necrosis factor-α (TNF-α), Interferon gamma (IFN-γ), Prostaglandin E2 (PGE2), Picibanil (OK-432), Poly IC, and a combination of two or more thereof, but is not limited thereto. The maturation factor may be treated together or at different times, for example, at intervals of 10 minutes to 24 hours, preferably at intervals of 8 hours to 24 hours, and more preferably at intervals of 15 to 22 hours. In an exemplary embodiment of the present invention, the OK-432 was treated at different times with different maturation factor, and the time difference is to prevent sensitization of the OK-432 with the antigen to induce a nonspecific immune response. In addition to this purpose, the time point for treatment between the maturation factors may be controlled to induce effective maturation of dendritic cells.

In some cases, a medium used for inducing the differentiation of dendritic cell precursor cells into immature dendritic cells may be a general medium used for culturing animal cells, for example, a serum-free medium as well as a serum-containing medium. For example, the medium contains serum (for example, fetal bovine serum, horse serum and human serum). The medium usable in the present invention includes, for example, RPMI series (for example, RPMI 1640), Eagle's MEM (Eagle's minimum essential medium, Eagle, H. Science 130:432 (1959)), α-MEM, Iscove's MEM, 199 medium, CMRL 1066, RPMI 1640, F12, DMEM (Dulbecco's modification of Eagle's medium, Dulbecco), a mixture of DMEM and F12, Way-mouth's MB752/1, McCoy's 5A and MCDB series, but is not limited thereto. In addition, as the serum-free medium, X-VIVO series (X-VIVO15, X-VIVO10, etc.) and CellGro, etc., may be used. The medium may contain other components, for example, an antioxidant (for example, (3-mercaptoethanol).

In some cases, when culturing the immature dendritic cell in the preparation method of according to the present invention, an mTOR inhibitor may be further treated in addition to the maturation factors.

The present inventors found that in the mature dendritic cell prepared by further treatment of the mTOR inhibitor, expression of cytokines IL-12 and IFN-γ could be increased, an immunity induction ability could be increased in cancer prevention models, and excellent anti-cancer effect could be exerted in cancer treatment models.

The mTOR inhibitor may include any type of inhibitor that directly binds to mTORC for inhibition or acts for competitive inhibition with ATP in a decomposition site of the mTORC, but for example, may be any one selected from the group consisting of rapamycin, sirolimus, everolimus, temsirolimus, ridaforolimus, NVP-BEZ235, SF-1126, XL-765, PKI-587, PF-04691502, PKI-402, OSI-027, AZD-8055, PP-242, PP-30, torin-1, WYE-125132, WAY-600, WYE-687, WYE-354, KU-0063794, and Palomid-529, but is not limited thereto.

Among them, the present inventors confirmed that the matured dendritic cell treated with rapamycin could increase the expression of IL-12, improve the Th1 immune response involved in IFN-γ, increase cytotoxic T lymphocytes and natural killer cells, and improve activities thereof.

The mTOR inhibitor may be treated at a concentration sufficient to obtain the mature dendritic cell having improved induction ability and function of the desired cytotoxic T lymphocyte, but for example, a concentration of the mTOR inhibitor may be 1 to 500 ng/mL, and preferably 1 to 450 ng/mL. Among the mTOR inhibitors, the rapamycin is preferably treated at a concentration of 1 to 10 ng/mL. Within the above-described range of concentration, it is possible to increase the expression of IL-12 and IFN-γ, increase cytotoxic T lymphocyte proliferation and activity. However, when the concentration exceeds 10 ng/mL, the T cell proliferation tends to decrease.

According to the preparation method of the present invention, it is possible to prepare the dendritic cell having remarkably improved cell permeability, an improved cytotoxic T lymphocyte induction ability, and an increased secretion ability of various cytokines such as IFN-γ, IL-12, etc. Above all, the dendritic cell prepared according to the preparation method strongly induces death of antigen-specific cancer cells (see FIGS. 2A through 2E).

Based on these results, it was confirmed that the immunity induction ability could be improved, and excellent anticancer effect based thereon could be exhibited, and therefore, the present invention provides the dendritic cell prepared by the preparation method, and an immunotherapeutic agent including the same, and an anti-tumor vaccine, or a pharmaceutical composition for treating tumors.

In another aspect, the present invention is a dendritic cell prepared by the above-described preparation method. The dendritic cell according to the present invention may exhibit the following characteristics:

(i) increase in chemokine responsive migration ability;

(ii) increase in IL-12 secretion ability when re-stimulating the dendritic cell;

(iii) increase in IFN-γ secretion ability of T cell upon T cell stimulation with the dendritic cell;

(iv) increase in cytotoxicity of T cell upon T cell stimulation with the dendritic cell;

(v) increase in cytotoxic T lymphocyte when inducing the cytotoxic T lymphocyte with the dendritic cell; or (vi) increase in antigen-specific functional T cell when co-culturing with the dendritic cell.

Based on these characteristics, the present invention relates to an immunotherapeutic agent including the dendritic cell. The immunotherapeutic agent according to the present invention may increase an immune response or may selectively increase a part of immune response desirable for treatment or prevention of specific diseases, infection or disorders.

Based on this, the present invention relates to an anti-tumor vaccine or a pharmaceutical composition for treating tumors, including the dendritic cell.

Based on the fact that the the dendritic cell has immunogenicity when tumor has rich potential antigens and antigens are presented by the dendritic cell, the dendritic cell according to the present invention is usable as the anti-tumor vaccines for preventing tumors or tumor therapeutics. The dendritic cell according to the present invention may increase the immunogenicity of an object, thereby preventing or suppressing tumor proliferation and/or metastasis in the object.

The antigen usable in the anti-tumor vaccines may be, for example, liver cancer-specific antigen or prostate cancer-specific antigen, but is not limited thereto. The liver cancer-specific antigen may be, for example, AFP (alpha-fetoprotein), GPC-3 (glypican-3), MAGE-1 (Melanoma-associated antigen 1), and the prostate cancer-specific antigen may be PCA (prostate cancer antigen), PAP (prostatic acid phosphatase) or PSA (prostate-specific antigen), but is not limited thereto.

The antigen of the vaccines including the dendritic cell usable in the present invention is all of antigens capable of binding to a cell membrane penetrating peptide, and may include inactivated tumor cells, tumor cell-associated genes, peptides or proteins produced by a gene recombinant method. When it is attempted to obtain the antigen by the gene recombinant method, a nucleotide sequence encoding the antigen may be known in the art, or a full length of the known sequence, or a part of the full length of the known sequence may be used. The nucleotide sequence encoding the antigen may be cloned into a vector so that the desired antigen is expressed.

The anti-tumor vaccine according to the present invention may include both an immunization method performed by a single administration and an immunization method performed by a continuous administration.

The pharmaceutically acceptable carrier contained in the pharmaceutical composition of the present invention, which is generally used in preparation, includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but the present invention is not limited thereto. The pharmaceutical composition of the present invention may further contain a lubricant, a wetting agent, a sweetening agent, an odorant, an emulsifier, a suspension, a preservative, and the like, in addition to the above components. Pharmaceutically acceptable carriers and formulations that are suitable are described in Remington's Pharmaceutical Sciences (19th ed., 1995) in detail.

An appropriate dosage of the pharmaceutical composition of the present invention may be variously prescribed depending on factors such as a formulation method, an administration manner, the age, body weight, sex, administration time and administration route of the patient. However, serious toxicity (Grade: 3 or more) depending on the dosage has not been reported, and thus, the dosage is largely determined depend on the preparation method and yield. Meanwhile, intradermal or subcutaneous dosage of the pharmaceutical composition of the present invention is preferably $0.1 \times 10^7$ to $10 \times 10^7$ cells.

The pharmaceutical composition of the present invention is prepared in a single dose form by formulation using a pharmaceutically acceptable excipient according to a method that may be easily performed by a person having ordinary skill in the art to which the present invention pertains. Here, the formulation may be in a form of suspension in a cell freezing medium, or a form of suspension in a buffer solution, and may additionally contain a stabilizer. The dendritic cell according to an exemplary embodiment of the present invention may be frozen after antigen sensitization, and thawed to be used if necessary. Stability of the dendritic cell according to an exemplary embodiment of the present invention was evaluated for 3 to 9 months, and it was confirmed that the function and stability of the dendritic cell were not significantly changed by freezing storage.

The pharmaceutical composition of the present invention is administered parenterally, and may be administered by intravenous injection, subcutaneous injection, intraperitoneal injection, transdermal administration, etc.

Hereinafter, the present invention will be described in more detail with reference to the following Examples. However, the following Examples are only for exemplifying the present invention, and it will be obvious to those skilled in the art that the scope of the present invention is not construed to be limited to these Examples.

Example 1: Preparation of Autologous Dendritic Cell (Ag—BH4h) (PBMC→imDC)

(1) Differentiation of Immature Dendritic Cell (imDC) from Peripheral Blood Mononuclear Cell (PBMC) (i.e., PBMC→imDC)

With regard to blood mononuclear cells of healthy individuals, peripheral blood mononuclear cells (PBMCs) were collected from which reticulocyte, granulocyte, platelet, plasma, etc. were removed, by performing density gradient centrifugation using Ficoll-Paque Plus (Endotoxin-free grade) at room temperature.

The peripheral blood mononuclear cells were taken and centrifuged to harvest the cells, and the cells were suspended in RPMI1640 medium containing autologous plasma at a certain concentration, and cultured in a cell incubator. When frozen PBMCs were used, the PBMCs were thawed and washed with HBSS or serum-free medium.

Monocytes were separated from the peripheral blood mononuclear cells using plastic adherency to a plastic ware, which is a common material of an animal cell incubator. Since the monocytes have high plastic adherency to a plastic ware which is the bottom material of a cell incubator, the peripheral blood mononuclear cells suspended in a medium were cultured at 37° C., and nonadherent cells were removed together with the medium, thereby obtaining adherent cells as a fraction in which patient's mononuclear cells were selectively adjusted to 80% or more of the total blood cell numbers.

A dendritic cell differentiation medium that induced dendritic cell differentiation from the monocytes was RPMI1640 medium to which cytokine mixture (Interleukin-4: IL-4 which is E. coli expressed human recombinant protein, JW CreaGene, final concentration: 300 ng/mL or less) and GM-CSF (JW CreaGene, final concentration: 100 ng/mL or less) were added.

(2) Immature Dendritic Cell

After three days from the start of the culture, cells floating from the bottom were collected and counted, and each aliquot was transferred to a culture vessel and prepared for maturation. Some cells were taken and the expression level of various markers expressed on the cell surfaces [HLA-DR (BD, Cat #555812), HLA-ABC BD, Cat #555552], CD40 (BD, Cat #555588), CD80 (BD, Cat #557227), CD86 (BD, Cat #555657) and CD83 (BD, Cat #556855)] were analyzed by flow cytometry (FACS).

(3) Induction of Maturation of Immature Dendritic Cell (imDC→mDC)

Maturation of the above immature dendritic cell of (2) was induced. That is, TNF-α(Tumor necrosis factor-α; Peprotech #300-01A, 10 ng/mL), IL-1β(Interleukin-1β; Peprotech #200-01B, 10 ng/mL), IL-6 (Interleukin-6; Peprotech #200-06, 10 ng/mL), PGE$_2$ (Prostaglandin E$_2$; Sigma #P0409, 1 µg/mL) were added at a predetermined concentration for maturation induction of the dendritic cell. The medium also contained IFN-γ (LG life science, final concentration: 30 to 1000 U/mL), and Poly IC (Sigma # P0913, final concentration: 10 µg/mL) known as a TLR (toll like receptor) signaling material as a dendritic cell maturation and activation factor, and as a cell-mediated immunity-inducing factor each at a predetermined concentration. Further, rapamycin (Santa Cruz # SC-3504) which is a mTOR inhibitor, was added to the medium at a concentration of 5-10 ng/mL.

In the presence of the above-described maturation factors, the immature dendritic cells were cultured for 12 hours to 48 hours, and then treated with picibanil (OK-432) (pharmaceutical drug, Picibanil, JW Pharmaceutical Corporation, final concentration: 1-2 µg/mL) and a cancer-specific antigen (CTP-GPC-$3_{33-559}$; 5 to 10 µg/mL, JW CreaGene) for cancer-specific immune response in each culture vessel each at a predetermined concentration, and cultured for 3 to 7 hours. The floating cells were collected as a final therapeutic agent, washed twice, and suspended in a cell freezing stabilizer (human serum albumin or human plasma containing DMSO) to complete a stock solution.

Comparative Example 1: Preparation of Autologous Dendritic Cell (Ag—O/N)

Dendritic cells were prepared in the same manner as in Example 1 except for simultaneously treating the immature dendritic cells with the maturation factor and antigen, and the time point at which the antigen is treated.

Test Example 1: Comparison of Biological Activity and Immunological Activity of CreaVax-HCC Autologous Dendritic Cell The migration ability and the IL-12 amount secreted in the culture media between respective dendritic cells after the maturation process when preparing the dendritic cells of Example 1 (Ag—BH4h; the antigen sensitization was performed at 4 hours before cell harvest which was the last stage of maturation process) and Comparative Example 1 (Ag—O/N; the antigen sensitization was performed together with maturation factor treatment at the immature stage) were measured, and shown in FIGS. 1A and 1B, respectively, and T cell proliferation and IFN-γ when co-culturing T cells isolated from peripheral blood cells and the dendritic cells of Example 1 and Comparative Example 1 were measured, and shown in FIGS. 1C and 1D, respectively. Here, the antigen was GPC-3 (SEQ ID NO: 15).

According to FIG. 1A, it could be confirmed that the migration ability of the dendritic cell of Example 1 was about 1.5 times larger than that of Comparative Example 1.

Specifically, MIP-3β (R&D systems, Cat. #361-MI-025) was prepared in RPMI 1640 medium containing 10% FBS so as to have a final concentration of 50 ng/mL, and 0.6 mL of the reaction material above was added to a lower chamber of a transwell (Coning, Cat #3422) having a pore size of 8.0 µm, and $5 \times 10^4$ matured dendritic cell was placed in an upper chamber and reacted at 37° C. for 120 minutes. Then, the dendritic cells migrated to the lower chamber by MIP-3β were counted and percentage of the migrated cells was calculated from the number of initially loaded cells. As a negative control group, a medium that was not treated with MIP-3β was used, and the remaining method was performed in the same manner as above.

In addition, in order to measure amounts of IL-12 and IL-10, IL-12 and IL-10 were analyzed by ELISA in the culture media in which the dendritic cells were secreted during antigen treatment and maturation. An experimental method was performed according to manual (IL-12; BD, Cat. #555183, IL-10; BD Cat. #555157) of the ELISA kit supplier. Results of the experiment were shown in FIG. 1B.

Figure 1B:
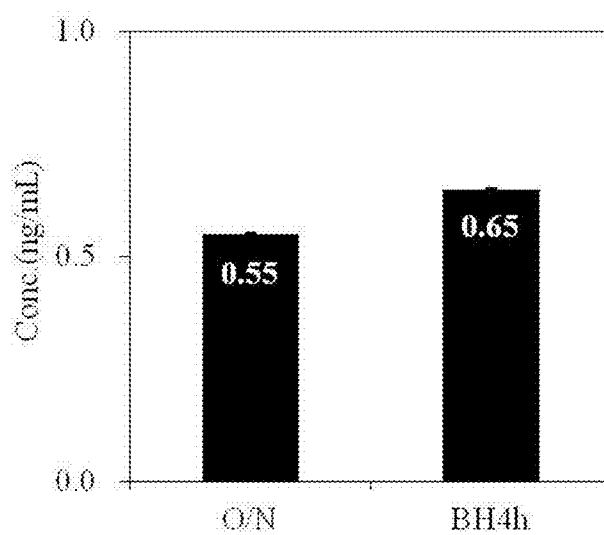

According to FIG. 1B, it could be confirmed that the amount of secreted IL-12 in the re-stimulated culture media of the dendritic cell according to Example 1 was about 20% higher than that of Comparative Example 1. It suggests that the dendritic cell according to an exemplary embodiment of the present invention more effectively induces Th1 immune response upon the reaction with T cells.

In addition, in order to measure T cell proliferation, T cells were isolated from the frozen peripheral mononuclear cells using a naive pan T cell isolation kit (MACS, Cat. #130-097-095). After thawing dendritic cells, the DCs were mixed with CFSE (carboxyfluorescein diacetate succinimidyl ester, Molecular Probes, cat. # MOP-C-1157)-labeled T cells at a ratio of 1:10 and culture for 5 days. For the CFSE staining, T cells were suspended at a concentration of $1\times10^6$/mL, and the CFSE was added to a final concentration of 10 µM, and the cells were reacted in 0.1% HSA/PBS buffer at 37° C. for 15 minutes. The cells were washed twice with RPMI 1640 medium and $1\times10^5$ T cells and $1\times10^4$ antigen-sensitized mature dendritic cells were triplicated in 96 well plates and cultured for 5 days. After culturing, the cells were collected and subjected to FACS analysis, and the proliferated cells were analyzed by $CFSE^{lo(w)}$ fraction. Experimental results thereof were shown in FIG. 1C.

Figure 1C:
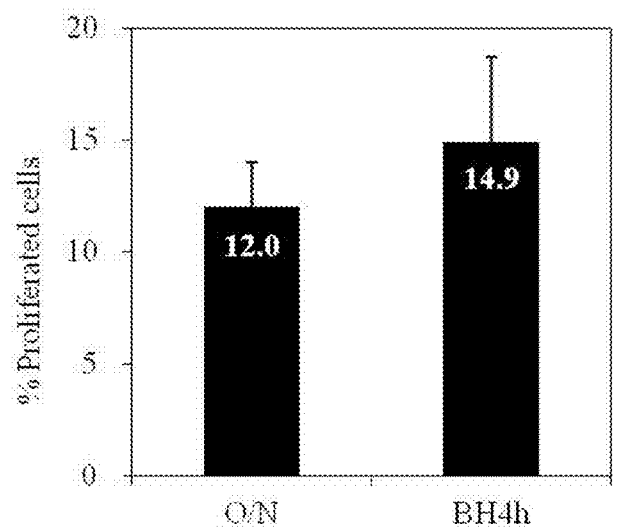

According to FIG. 1C, it could be confirmed that the T cell proliferation of the dendritic cell according to Example 1 was about 24% higher than that of the dendritic cell prepared in Comparative Example 1.

The autologous T cells and dendritic cell were cultured for 5 days, and IFN-γ in the culture supernatant was analyzed by ELISA (BD Cat. #555142). Results thereof were shown in FIG. 1D.

Figure 1D:
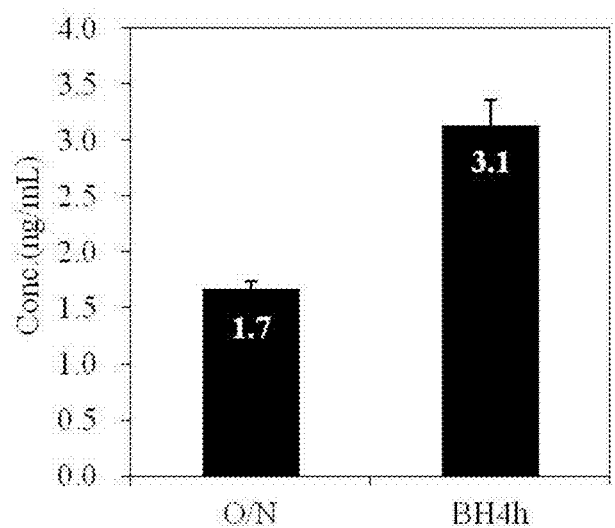

According to FIG. 1D, it could be confirmed that an IFN-γ secretion amount in the culture media in which the dendritic cell according to Example 1 was cultured together with the T cell was about 2 times larger than that of the culture media in which the dendritic cell prepared in Comparative Example 1 was cultured together with the T cell.

Test Example 2: Activity Test of Cytotoxic T Lymphocyte (CTL) Induced by Autologous Dendritic Cell Cytotoxic T lymphocytes (CTL) were induced by the mixed reaction of autologous T cell (isolated from PBMCs) and dendritic cells of Example 1 (Ag—BH4h) and Comparative Example 1 (Ag—O/N). Here, the antigen was GPC-3. T cells were isolated from the peripheral blood cells of the same human used for the preparation of dendritic cells using a naive T cell isolation kit (MACS, Cat. #130-097-095). The matured dendritic cells and the isolated T cells were mixed at a ratio of 1:10 ($4\times10^5$:$4\times10^6$) and cultured for 6 to 7 days. The primarily stimulated T cells were collected and re-stimulated at the same ratio (1:10) as dendritic cells sensitized with antigen. The culture medium (RPMI1640+ 10% AB serum) was supplemented or exchanged with fresh media every 2 to 3 days to provide a suitable culture environment. At the first stimulation, IL-7 (Peprotech, Cat. #200-07) was added at a concentration of 5 ng/mL. From the second stimulation, IL-7 was treated at the same concentration from 2 to 3 days after culture, and then, IL-2 (Proleukin, Novartis) was treated at a concentration of 50 U/mL. With respect to the CTLs induced by stimulating the T cells two to three times with the antigen-sensitized dendritic cells, the number of CTL cells was confirmed (FIG. 2A) and activity test of the CTL (cytotoxicity, FIG. 2B) was analyzed. That is, when co-culturing the T cell and the dendritic cell during the CTL induction, on the next day of stimulation, the IFN-γ secretion amount was measured by taking a part of the supernatant using an ELISA method. Results thereof were shown in FIG. 2B.

Figure 2A:
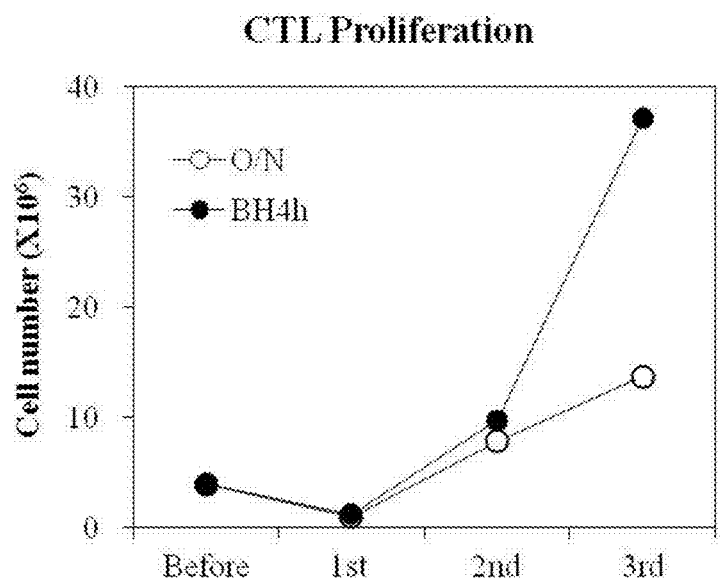
FIGS. 2A through 2E show results as follows.
Figure 2B:
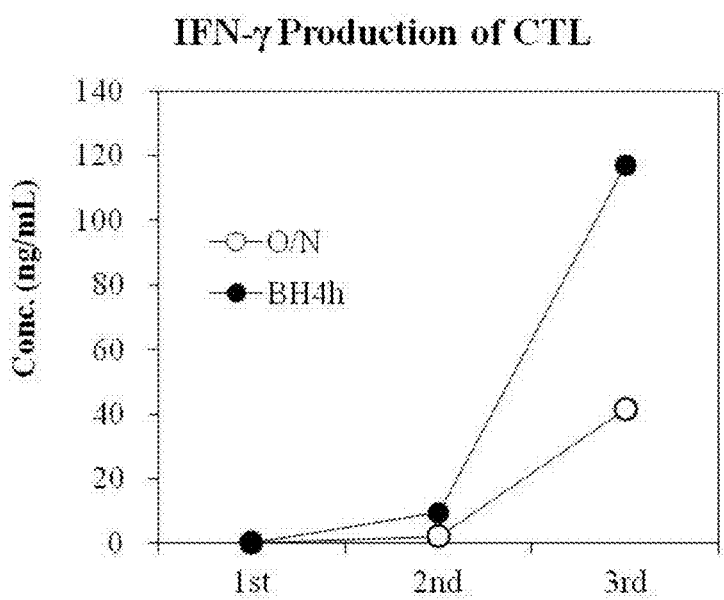
Figure 2C:
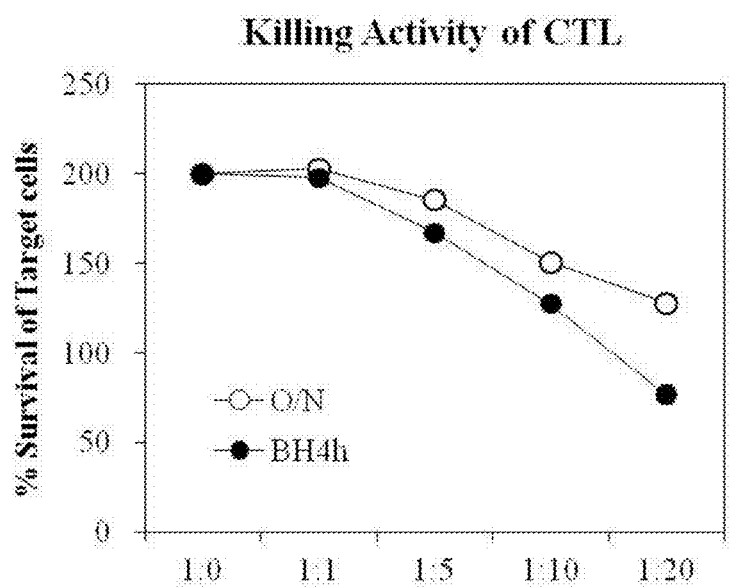
Figure 2D:
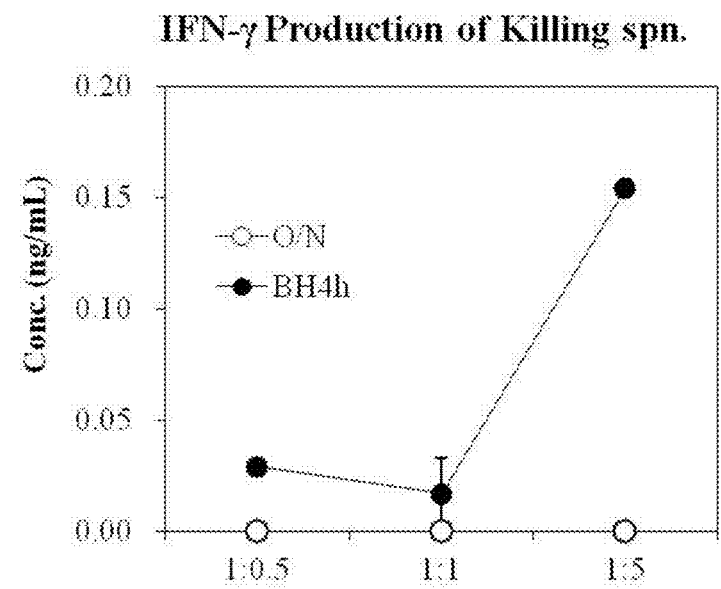

As a target cell of cytotoxicity, a Hep G2 cell line matching the HLA type and expressing antigen (GPC3) was used. The target cells and the effector cells (CTL) were mixed at 1:0, 1:1, 1:5, 1:10 or 1:20, and cultured for 20 to 24 hours, and culture media were collected and frozen for measuring IFN-γ, and plates were fixed with 10% formalin for 1 hour. Then, 200 μL of 0.4% crystal violet was added to each well and stained for 30 minutes. Then, the plates were washed three times and dried at room temperature. After drying, 100 μL of 80% methanol was added thereto, followed by reaction for 20 minutes. Absorbance was measured at 570 nm to confirm cytotoxicity (FIG. 2C). Further, the target cells and the effector cells (CTL) were mixed at 1:0.5, 1:1, 1:5 and cultured for 20 to 24 hours. Then, the IFN-γ secretion amount was measured by ELISA using the culture supernatant (FIG. 2D).

According to FIGS. 2A through 2D, it could be confirmed that the number of cytotoxic T lymphocytes induced by the dendritic cell according to Example 1 was two times or higher than the number of cytotoxic T lymphocytes induced by the dendritic cell according to Comparative Example 1, and the IFN-γ secretion amount in the culture media of Example 1 was two times or higher, and the cytotoxicity was 1.5 times or higher, and the IFN-γ secretion amount in the culture media was remarkably increased in the culture media compared to those of Comparative Example 1.

In addition, in order to confirm the antigen-specific immune response of the GPC-3 antigen with respect to the active T cells induced by each dendritic cell, antigen-specificity of the CTL induced by the dendritic cells of Example 1 (Ag—BH4h) and Comparative Example 1 (Ag—O/N) was analyzed by IFN-γ ELISPOT (BD, Cat. #551849). Specifically, in order to confirm the antigen specificity, two kinds of dendritic cells treated without or with the antigen were prepared. Here, a dendritic cell that is not treated with Picibanil (OK-432) was prepared to lower non-specific reaction. 1×10⁴ of induced active T cells and 3×10³ of dendritic cells were cultured in a 3:1 ratio for 18 to 24 hours in a cell culture incubator, and ELISPOT analysis was performed according to a method presented in the kit. The number of spots measured at the time of the reaction with the dendritic cell not treated with the antigen in the analysis was subtracted, and results thereof are shown in FIG. 2E.

Figure 2E:
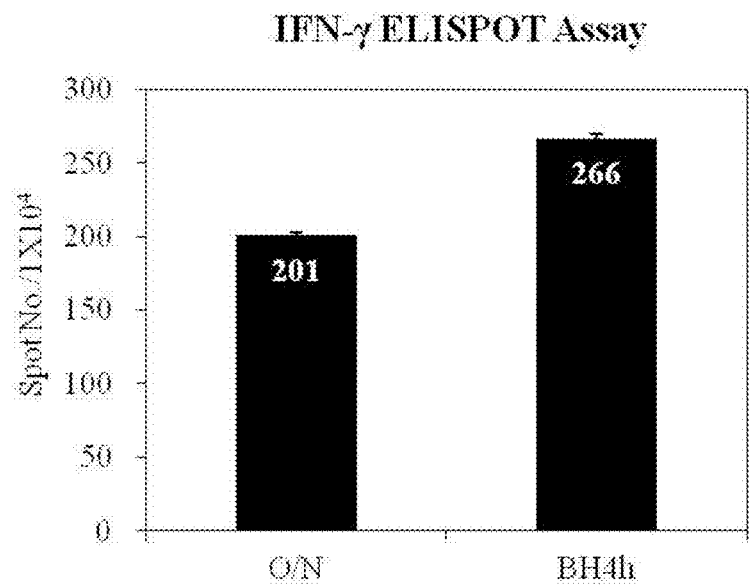

According to FIG. 2E, it could be confirmed that the antigen specificity of the active T cells induced by the dendritic cell according to Example 1 was increased by 30% or more.

Test Example 3: Cell Surface Phenotype of Autologous Dendritic Cell

In order to perform phenotypic analysis of the immature dendritic cell and the dendritic cells of Example 1 (Ag— BH4h) and Comparative Example 1 (Ag—O/N), the dendritic cells were suspended in FACS buffer (PBS+0.1% sodium azide+1% FBS) and prepared in 3 to 5×10⁴ cells per FACS tube. Here, the antigen was GPC-3. Then, 3 μL of FACS antibodies with respect to HLA-DR, HLA-ABC, CD80, CD86, CD40, CD83 [HLA-DR (BD, Cat #555812), HLA-ABC BD, Cat #555552], CD40 (BD, Cat #555588), CD80 (BD, Cat #557227), CD86 (BD, Cat #555657), and CD83 (BD, Cat #556855)] were added and reacted at 4° C. for 20 minutes. After the reaction, cells were washed with FACS buffer, and cell phenotypic analysis was performed. Expression on the HLA-DR, HLA-ABC, CD80, CD86, CD40, and CD83 which are phenotypes of the matured dendritic cells was confirmed. Results thereof were shown in FIG. 3 and Table 1 below.

Referring to FIG. 3, it could be confirmed that the expression of CD80 and CD83 was low in the immature dendritic cell. Meanwhile, the expression of CD80/CD83 was significantly increased in the dendritic cell which was matured by treating the immature dendritic cell with the maturation factor as in Example 1 and Comparative Example 1 as compared to that of the immature dendritic cell, and a maturation level was not significantly changed by the difference of antigen sensitization time.

TABLE 1

| | Positive cells (%), Mean ± SD | | | | | |
|---|---|---|---|---|---|---|
| | HLA-DR | CD86 | HLA-ABC | CD80 | CD83 | CD40 |
| imDC | 81.0 ± 11.4 | 85.3 ± 14.2 | 98.4 ± 2.8 | 12.9 ± 6.3 | 4.6 ± 2.9 | 83.5 ± 16.6 |
| BH4h | 97.4 ± 2.2 | 98.9 ± 1.1 | 99.4 ± 1.0 | 97.1 ± 2.1 | 77.8 ± 14.1 | 98.1 ± 2.4 |
| mDC | 98.3 ± 1.2 | 98.9 ± 1.0 | 99.5 ± 0.5 | 97.4 ± 1.6 | 89.6 ± 7.2 | 97.6 ± 1.7 |

Test Example 4: Functional Evaluation of Dendritic Cell Depending on Presence or Absence of CTP The CTLs were induced according to the methods of Test Example 1, Test Example 2, and Test Example 3, and functional evaluation depending on presence or absence of the CTP was performed. The antigen with the CTP was named with CTP-Ag, and the antigen without the CTP was named with X—Ag. Here, the antigen was GPC-3. Results obtained by confirming the dendritic cell phenotype were shown in FIG. 4A. The autologous T cells and the dendritic cells according to Example 1 or Comparative Example 1 were co-cultured for 5 days, and the IFN-γ in the culture media was analyzed by ELISA, and results thereof were shown in FIG. 4B. The CTLs were induced and CD8 positive cells were analyzed and shown in FIG. 4C, and the IFN-γ in the supernatant was measured by ELISA, and shown in FIG. 4D. The antigen-specific immune response with respect to the active T cells induced by each dendritic cell sensitized with the GPC-3 antigen was analyzed by IFN-γ ELISPOT, and results thereof were shown in FIG. 4E.

Figure 4A:
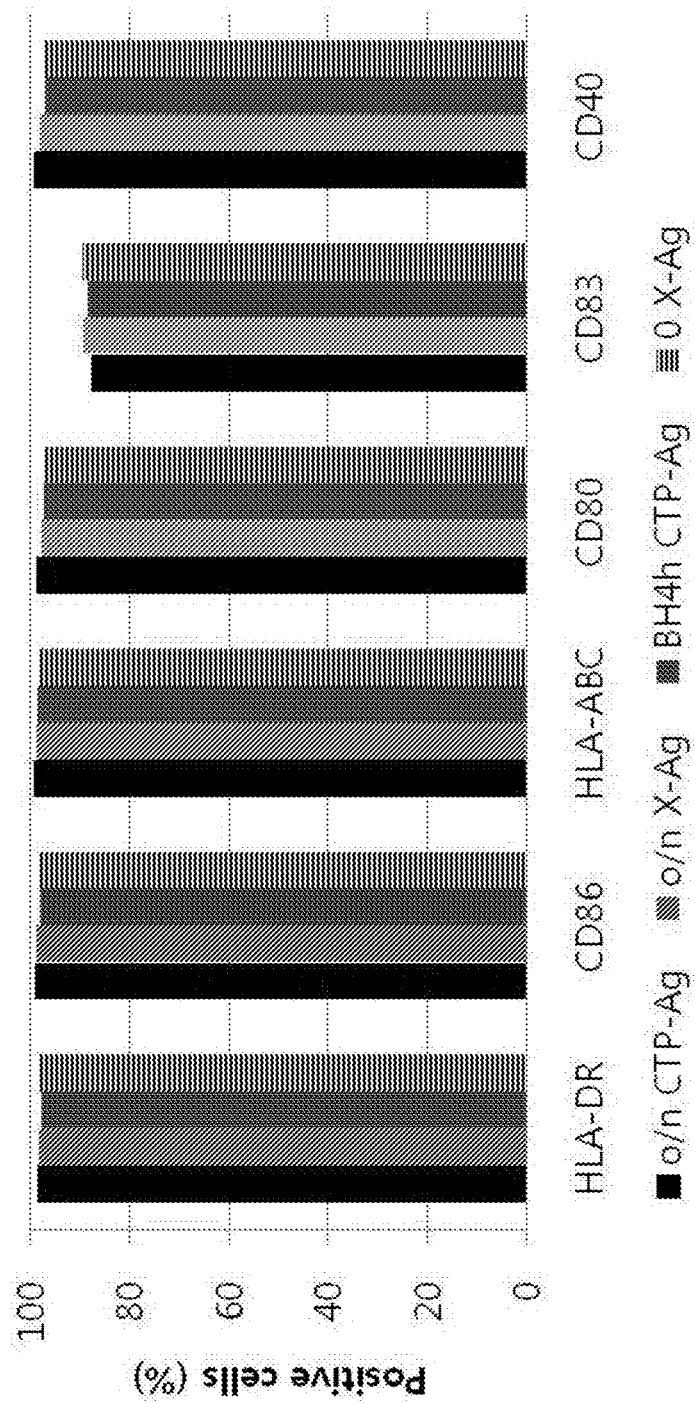
FIGS. 4A through 4F show results as follows.
Figure 4B:
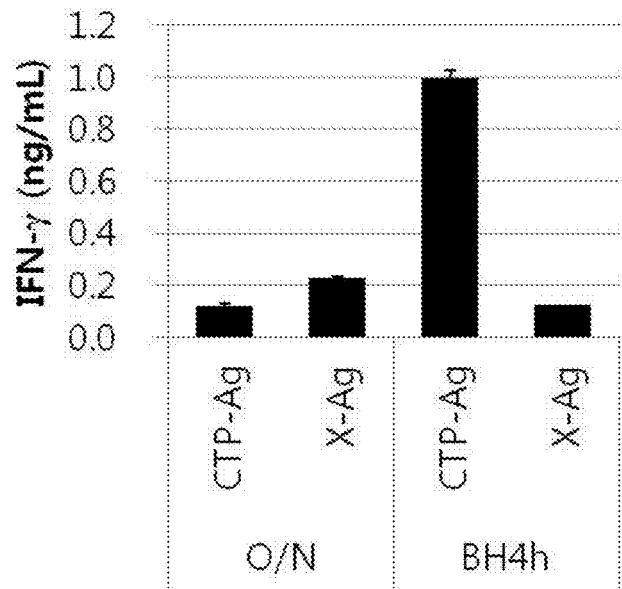
Figure 4C:
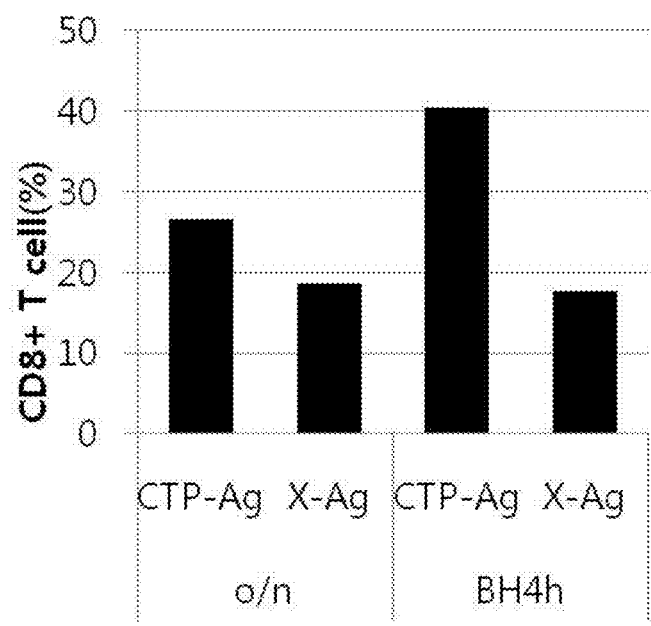
Figure 4D:
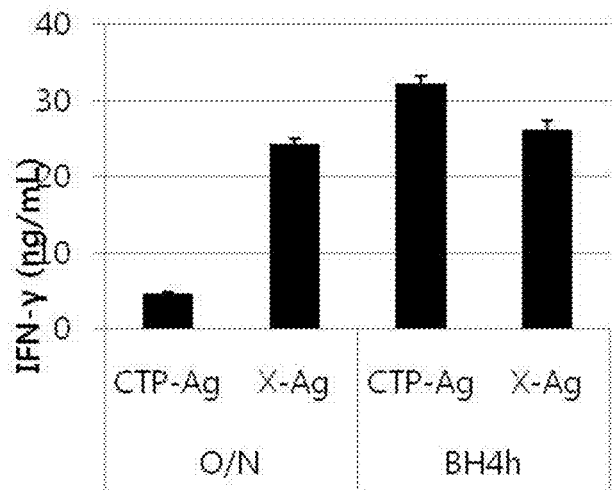
Figure 4E:
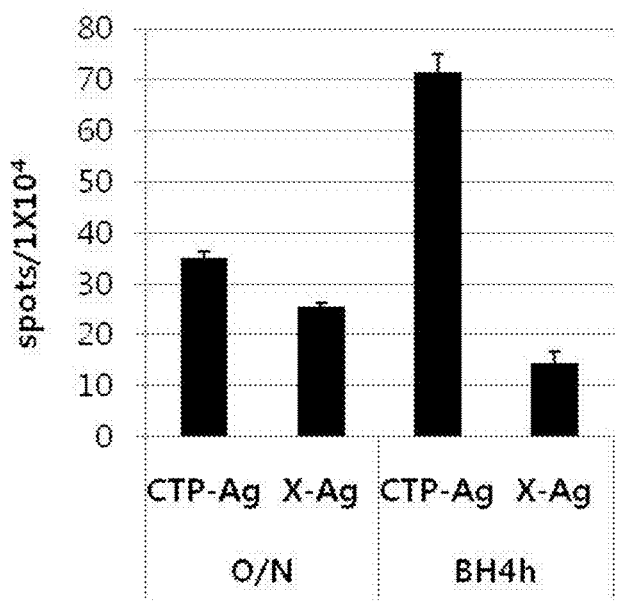

According to FIGS. 4A through 4E, when comparing a case in which the dendritic cell is treated with the maturation factor, and then, is sensitized with the antigen bound to the cell membrane penetrating peptide at 4 hours before cell harvest, and a case in which the dendritic cell is treated with the maturation factor, and then, is sensitized with the antigen to which the cell membrane penetrating peptide is not bound, there was no significant change in the phenotype of the two dendritic cells (FIG. 4A). However, when co-culturing with T cells, the amount of IFN-γ was increased by 5 times or more (FIG. 4B), the number of CD8+ T cells was increased by 2 times or more (FIG. 4C), the level of IFN-γ indicating activation of CD8+ T cells was increased by 30% or more (FIG. 4D), and the number of ELISPOT was increased by 5 times or more (FIG. 4E). Therefore, it could be confirmed that even when the dendritic cells were sensitized with the same antigen under the same conditions, the immunity induction ability of the dendritic cell sensitized with the antigen bound to the cell membrane penetrating peptide was remarkably improved.

As a part of the cytotoxic activity test, intra-cellular staining was performed to confirm the expression level of granule (Granzyme B) secreted when the active T cell met the target cells. Specifically, after stimulation, the CTLs were obtained, washed, and the target cells (HepG2) were added at a ratio, i.e., target cell (HepG2):CTL of 1:20, wherein GolgiStop (BD, Cat #) was added together at an amount of 0.14 µL per 200 µL of cell culture media, and stimulated at 37° C. for 4 to 5 hours. The cells were collected and washed, and PBS containing 10% human serum was added for Fc receptor blocking. After culturing at 4° C. for 15 minutes, and then the antigens on the cell surface were stained with CD3 (BD, Cat. #555335) and CD4 (BD, Cat. #555346), CD8 (BD, Cat. #555367) at 4° C. for 20 minutes. The cells were reacted with 250 µL of Fixation/Permeabilization solution (BD, Cat. #554715) at 4° C. for 20 minutes, and then washed twice with Perm/Wash buffer, and stained with granzyme B (BD, Cat. #561142) for 30 to 50 minutes, washed and analyzed by flow cytometry. Results thereof were shown in FIG. 4F.

Figure 4F:
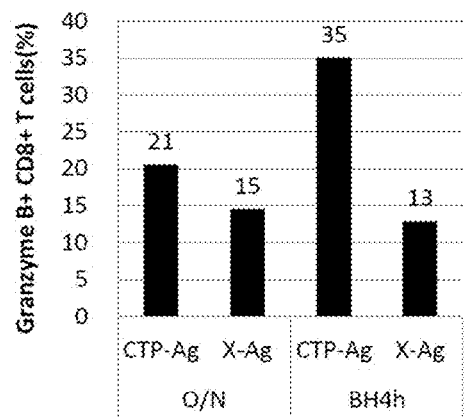

According to FIG. 4F, it could be confirmed that the granule (Granzyme B) secretion which shows to confirm the cytotoxic activity of the active T cells was increased 2 times or more when the antigen bound to the cell membrane penetrating peptide was sensitized. It was confirmed that the granule (Granzyme B) was more highly expressed when the antigen bound to the cell membrane penetrating peptide was treated after the treatment with the maturation factor as compared to the case in which the antigen bound to the cell membrane penetrating peptide was treated in the immature dendritic cell.

Test Example 5: Antigen Uptake Ability of Dendritic Cell Depending on Presence or Absence of CTP In order to confirm an antigen uptake ability of the immature dendritic cell and the mature dendritic cell of Example 1 (Ag—BH4h), an uptake ability of rhodamine-labeled antigen (PSA antigen, SEQ ID NO: 16) was analyzed. In addition, in order to confirm the antigen uptake ability of the immature dendritic cell or the mature dendritic cell, a dextran-uptake assay which is the most commonly used was performed together. The rhodamine-labeled antigen was prepared as follows. First, NHS-Rhodamine (Pierce) was dissolved in DMSO (Sigma) at a concentration of 10 mg/mL, and mixed and reacted with 1 mg/mL protein for 1 hour. A precipitate was removed by centrifugation, and NHS-Rhodamine that was not reacted was removed by gel filtration chromatography (GE, Sephadex G-25, 17-0033-02). The labeled protein was identified at Ex/Em=552/575 nm using HPLC (Agilent, 1200 series), and protein quantification was calculated by measuring absorbance at 280/555 nm with a spectrophotometer (Agilent, 8453 series).

Specifically, the immature dendritic cell ($1\times10^5$ cell) on the third day after culturing and the mature dendritic cell that was not sensitized with the antigen on the fourth day after culturing were obtained, wherein the cells were cultured in the same manner as in the culture condition of the immature dendritic cell of Example 1, and centrifuged, and suspended in dendritic cell culture media each having 100 µL, and placed in FACS tubes. Among them, a cell used as a negative control group was placed in ice for 30 minutes in advance to be arrested. The cells were treated with rhodamine fluorescently conjugated CTP-PSA and X-PSA (PSA without CTP) at a concentration of 20 µg/mL for 1 hour, and washed to perform flow cytometry. Analysis results were shown with median of the fluorescent intensity, and results thereof were shown in FIG. 5.

Further, in order to re-examine the general difference in antigen uptake ability of the immature dendritic cell and the mature dendritic cell used in the test, the cells were treated with 10 µL of FITC fluorescently conjugated dextran (Sigma, Cat. #FD-40S) each at 37° C., and the negative control group was reacted at 4° C. for 1 hour. The cells were washed with FACS buffer (PBS+0.1% sodium azide+1% FBS), and histogram analysis was performed on the FACSDiva (BD) program which is FACS analysis program, to obtain a single fluorescence histogram specifying FL-1 on an X axis. Here, linear segmentation was performed to set a region in which 97% of negative fluorescent standard sample is present as a negative fluorescence region, and in this state, region states for each section were performed, and single positive fluorescent (Dextran-FITC+phenotype) segmentation ratio of each sample was obtained and analyzed. Results thereof were shown in FIG. 5.

Figure 5:
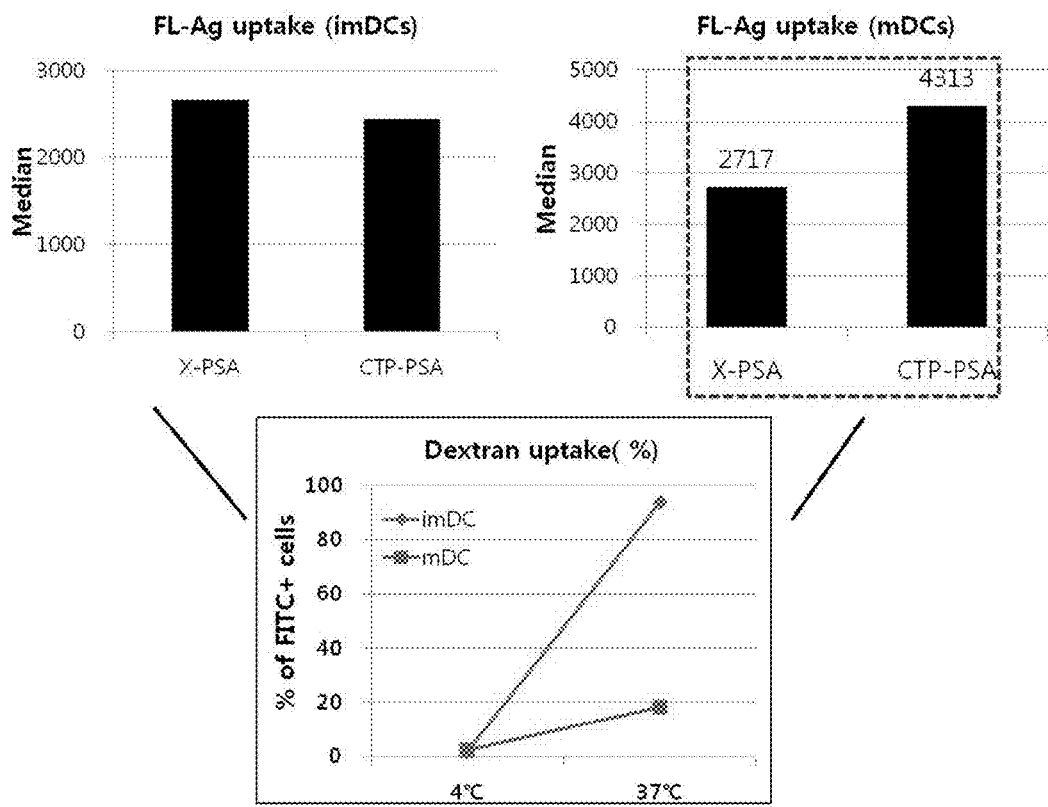
FIG. 5 shows comparative analysis results of antigen (CTP-PSA or X-PSA) uptake ability between immature dendritic cells (imDCs) and mature dendritic cells (mDCs) using Rhodamine-labeled Ag.

According to FIG. 5, it could be reconfirmed that in the case of the immature dendritic cell, the antigen was well delivered into the dendritic cell, regardless of whether the cell membrane penetrating peptide was bound to the antigen. However, in the case of the matured dendritic cell, the antigen bound to the cell membrane penetrating peptide was more effectively delivered into the cell. That is, the present invention demonstrates that the delivery of the antigen into the dendritic cell was remarkably increased by the antigen sensitization at the maturation stage and the cell membrane penetrating peptide bound to the antigen, and thus, the functions of the dendritic cell were remarkably increased.

Figure 6A:
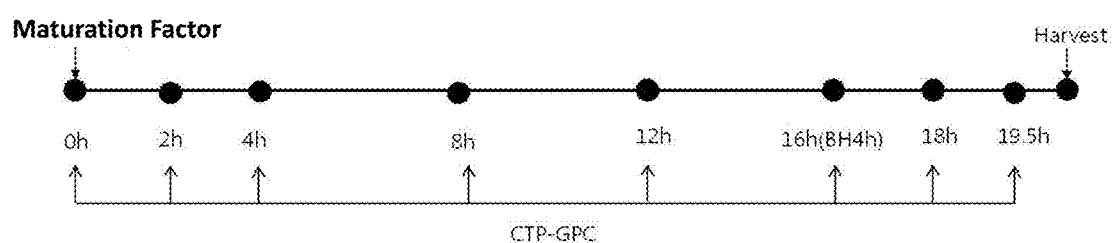
FIGS. 6A and 6B show comparative analysis results of an immune activity of the dendritic cell according to CTP-antigen treatment time.

Test Example 6: Functional Evaluation of Dendritic Cell According to CTP-Antigen Treatment Time The CTP-GPC3 was subdivided from the time point at which the maturation factor is treated to the time point at which the matured dendritic cells are harvested including Example 1 (Ag—BH4h; 16h) and Comparative Example 1 (Ag—O/N; 0h), and treated as in FIG. 6A. The test method described in FIG. 6A is different from the method for preparing the dendritic cell of Example 1 in view of the antigen treatment time, and other culturing conditions were applied in the same manner. The cells were sensitized with 5 µg/mL of CTP-GPC3 per time (0, 2, 4, 8, 12, 16, 18, 19.5 hours) after the time point at which the maturation factor is treated, and all cells were harvested at 20 hours after time point at which the maturation factor is treated. The time point at which the antigen is treated is 0 hour, which indicates O/N, and the time point at which the antigen is treated is 16 hour, which indicates BH4h. The autologous T cell and the dendritic cell were cultured for 5 days, and then, the IFN-γ in the culture media was analyzed by ELISA, and results thereof were shown in FIG. 6B.

Figure 6B:
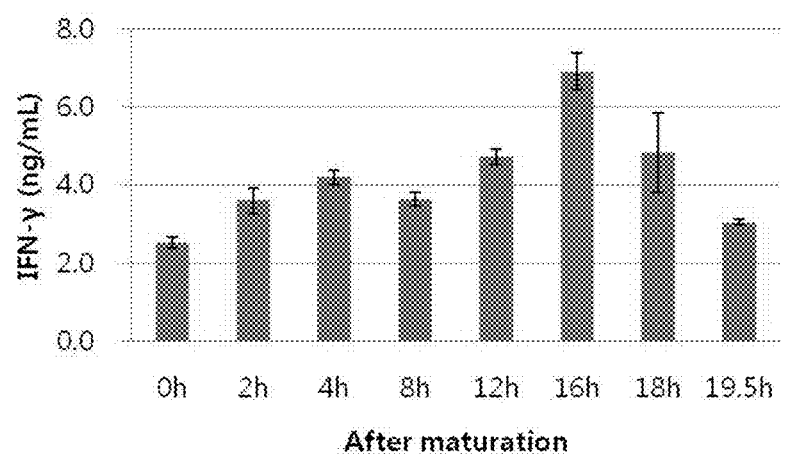

According to FIGS. 6A and 6B, it is considered that the CTP-antigen treatments when the time for CTP-antigen treatment is long (antigen treatment at 0, 2, 4 and 8 hours after the treatment with the maturation factor) and when the time for CTP-antigen treatment is very short (antigen treatment at 19.5 hours after the treatment with the maturation factor) showed a relatively low level of IFN-γ, and thus, it was not effective on immunologically active function of the dendritic cell. On the other hand, it could be confirmed that the dendritic cell sensitized with CTP-Ag at 12 hours to 18 hours after the treatment with the maturation factor, the immune activity was increased by secreting a large amount of IFN-γ which is a Th1 cytokine.

INDUSTRIAL APPLICABILITY

According to the method for preparing a dendritic cell of the present invention, it is possible to prepare dendritic cells having remarkably improved cell permeability, an improved cytotoxic T lymphocyte induction ability, and an increased secretion ability of various Th1 prone cytokines such as IFN-γ, IL-12, etc. The dendritic cells prepared according to the method of the present invention may exhibit an increase in immunity induction ability, and an excellent anti-cancer effect, which may be effectively usable for anti-tumor vaccines, or for compositions for treating tumors.

The invention claimed is:

1. A method for preparing a dendritic cell, comprising:
   culturing an immature dendritic cell to a mature dendritic cell with treating by 1-10 ng/mL of rapamycin and a maturation factor; and
   after maturation of the immature dendritic cell to the mature dendritic cell has been completed, sensitizing the mature dendritic cell with an antigen bound to a peptide having cell permeability,
   wherein said sensitizing of the mature dendritic cell with the antigen bound to the peptide having cell permeability is performed at least 6 hours and up to 48 hours after said treating by the maturation factor, and
   wherein said sensitizing of the mature dendritic cell with the antigen bound to the peptide having cell permeability is performed for 1 to 8 hours.

2. The method according to claim 1, wherein the peptide having cell permeability comprises a cytoplasmic transduction peptide (CTP).

3. The method according to claim 1, wherein the mature dendritic cell is sensitized in said sensitizing with the antigen bound to the peptide having cell permeability, so that an expression level of CD80, CD83, or CD40 is increased by 60% or more, compared to that of the immature dendritic cell.

* * * * *

UNITED STATES PATENT AND TRADEMARK OFFICE
CERTIFICATE OF CORRECTION

PATENT NO. : 10,478,479 B2
APPLICATION NO. : 15/327933
DATED : November 19, 2019
INVENTOR(S) : Yoon Lee Page 1 of 1

It is certified that error appears in the above-identified patent and that said Letters Patent is hereby corrected as shown below:

In the Specification

Column 7, Line 44: "3-mercaptoethanol" should be -- β-mercaptoethanol --.

Signed and Sealed this
Thirty-first Day of December, 2019

Andrei Iancu
*Director of the United States Patent and Trademark Office*

SEQUENCE LISTING

```
<160> NUMBER OF SEQ ID NOS: 16

<210> SEQ ID NO 1
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 1

Tyr Gly Arg Arg Ala Arg Arg Arg Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 2

Tyr Gly Arg Arg Ala Arg Arg Arg Ala Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 3

Tyr Gly Arg Arg Ala Arg Arg Ala Ala Arg Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 4

Tyr Lys Arg Lys Ala Arg Arg Ala Ala Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Cytoplasmic transduction peptide
```

```
<400> SEQUENCE: 5

Tyr Ala Arg Lys Ala Arg Arg Ala Ala Arg Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 6

Tyr Lys Arg Ala Ala Arg Arg Ala Ala Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 7

Tyr Glu Arg Glu Ala Arg Arg Ala Ala Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 8

Tyr Ala Arg Glu Ala Arg Arg Ala Ala Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 9

Tyr Gly Arg Ala Ala Arg Arg Ala Ala Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 10

Tyr Arg Arg Ala Ala Arg Arg Ala Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Cytoplasmic transduction peptide
```

```
<400> SEQUENCE: 11

Tyr Pro Arg Ala Ala Arg Ala Ala Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 12

Pro Ala Arg Ala Ala Arg Arg Ala Ala Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 13

Tyr Gly Arg Arg Arg Arg Arg Arg Arg Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Cytoplasmic transduction peptide

<400> SEQUENCE: 14

Tyr Arg Arg Arg Arg Arg Arg Arg Arg Arg
1               5                   10

<210> SEQ ID NO 15
<211> LENGTH: 527
<212> TYPE: PRT
<213> ORGANISM: Artificial Sequence
<220> FEATURE:
<223> OTHER INFORMATION: GPC-3

<400> SEQUENCE: 15

Ala Thr Cys His Gln Val Arg Ser Phe Phe Gln Arg Leu Gln Pro Gly
1               5                   10                  15

Leu Lys Trp Val Pro Glu Thr Pro Val Pro Gly Ser Asp Leu Gln Val
            20                  25                  30

Cys Leu Pro Lys Gly Pro Thr Cys Cys Ser Arg Lys Met Glu Glu Lys
        35                  40                  45

Tyr Gln Leu Thr Ala Arg Leu Asn Met Glu Gln Leu Leu Gln Ser Ala
    50                  55                  60

Ser Met Glu Leu Lys Phe Leu Ile Ile Gln Asn Ala Ala Val Phe Gln
65                  70                  75                  80

Glu Ala Phe Glu Ile Val Val Arg His Ala Lys Asn Tyr Thr Asn Ala
                85                  90                  95

Met Phe Lys Asn Asn Tyr Pro Ser Leu Thr Pro Gln Ala Phe Glu Phe
            100                 105                 110

Val Gly Glu Phe Phe Thr Asp Val Ser Leu Tyr Ile Leu Gly Ser Asp
        115                 120                 125

Ile Asn Val Asp Asp Met Val Asn Glu Leu Phe Asp Ser Leu Phe Pro
```

130                 135                 140
Val Ile Tyr Thr Gln Leu Met Asn Pro Gly Leu Pro Asp Ser Ala Leu
145                 150                 155                 160

Asp Ile Asn Glu Cys Leu Arg Gly Ala Arg Arg Asp Leu Lys Val Phe
                165                 170                 175

Gly Asn Phe Pro Lys Leu Ile Met Thr Gln Val Ser Lys Ser Leu Gln
            180                 185                 190

Val Thr Arg Ile Phe Leu Gln Ala Leu Asn Leu Gly Ile Glu Val Ile
            195                 200                 205

Asn Thr Thr Asp His Leu Lys Phe Ser Lys Asp Cys Gly Arg Met Leu
210                 215                 220

Thr Arg Met Trp Tyr Cys Ser Tyr Cys Gln Gly Leu Met Met Val Lys
225                 230                 235                 240

Pro Cys Gly Gly Tyr Cys Asn Val Val Met Gln Gly Cys Met Ala Gly
                245                 250                 255

Val Val Glu Ile Asp Lys Tyr Trp Arg Glu Tyr Ile Leu Ser Leu Glu
            260                 265                 270

Glu Leu Val Asn Gly Met Tyr Arg Ile Tyr Asp Met Glu Asn Val Leu
            275                 280                 285

Leu Gly Leu Phe Ser Thr Ile His Asp Ser Ile Gln Tyr Val Gln Lys
290                 295                 300

Asn Ala Gly Lys Leu Thr Thr Thr Ile Gly Lys Leu Cys Ala His Ser
305                 310                 315                 320

Gln Gln Arg Gln Tyr Arg Ser Ala Tyr Tyr Pro Glu Asp Leu Phe Ile
                325                 330                 335

Asp Lys Lys Val Leu Lys Val Ala His Val Glu His Glu Glu Thr Leu
            340                 345                 350

Ser Ser Arg Arg Arg Glu Leu Ile Gln Lys Leu Lys Ser Phe Ile Ser
            355                 360                 365

Phe Tyr Ser Ala Leu Pro Gly Tyr Ile Cys Ser His Ser Pro Val Ala
370                 375                 380

Glu Asn Asp Thr Leu Cys Trp Asn Gly Gln Glu Leu Val Glu Arg Tyr
385                 390                 395                 400

Ser Gln Lys Ala Ala Arg Asn Gly Met Lys Asn Gln Phe Asn Leu His
                405                 410                 415

Glu Leu Lys Met Lys Gly Pro Glu Pro Val Val Ser Gln Ile Ile Asp
            420                 425                 430

Lys Leu Lys His Ile Asn Gln Leu Leu Arg Thr Met Ser Met Pro Lys
            435                 440                 445

Gly Arg Val Leu Asp Lys Asn Leu Asp Glu Glu Gly Phe Glu Ser Gly
450                 455                 460

Asp Cys Gly Asp Asp Glu Asp Glu Cys Ile Gly Gly Ser Gly Asp Gly
465                 470                 475                 480

Met Ile Lys Val Lys Asn Gln Leu Arg Phe Leu Ala Glu Leu Ala Tyr
                485                 490                 495

Asp Leu Asp Val Asp Asp Ala Pro Gly Asn Ser Gln Gln Ala Thr Pro
            500                 505                 510

Lys Asp Asn Glu Ile Ser Thr Phe His Asn Leu Gly Asn Val His
            515                 520                 525

<210> SEQ ID NO 16
<211> LENGTH: 244
<212> TYPE: PRT
<213> ORGANISM: Artificial Sequence

```
<220> FEATURE:
<223> OTHER INFORMATION: PSA

<400> SEQUENCE: 16

Ala Pro Leu Ile Leu Ser Arg Ile Val Gly Gly Trp Glu Cys Glu Lys
1               5                   10                  15

His Ser Gln Pro Trp Gln Val Leu Val Ala Ser Arg Gly Arg Ala Val
            20                  25                  30

Cys Gly Gly Val Leu Val His Pro Gln Trp Val Leu Thr Ala Ala His
        35                  40                  45

Cys Ile Arg Asn Lys Ser Val Ile Leu Leu Gly Arg His Ser Leu Phe
    50                  55                  60

His Pro Glu Asp Thr Gly Gln Val Phe Gln Val Ser His Ser Phe Pro
65                  70                  75                  80

His Pro Leu Tyr Asp Met Ser Leu Leu Lys Asn Arg Phe Leu Arg Pro
                85                  90                  95

Gly Asp Asp Ser Ser His Asp Leu Met Leu Leu Arg Leu Ser Glu Pro
                100                 105                 110

Ala Glu Leu Thr Asp Ala Val Lys Val Met Asp Leu Pro Thr Gln Glu
            115                 120                 125

Pro Ala Leu Gly Thr Thr Cys Tyr Ala Ser Gly Trp Gly Ser Ile Glu
        130                 135                 140

Pro Glu Glu Phe Leu Thr Pro Lys Lys Leu Gln Cys Val Asp Leu His
145                 150                 155                 160

Val Ile Ser Asn Asp Val Cys Ala Gln Val His Pro Gln Lys Val Thr
                165                 170                 175

Lys Phe Met Leu Cys Ala Gly Arg Trp Thr Gly Gly Lys Ser Thr Cys
                180                 185                 190

Ser Gly Asp Ser Gly Gly Pro Leu Val Cys Asn Gly Val Leu Gln Gly
            195                 200                 205

Ile Thr Ser Trp Gly Ser Glu Pro Cys Ala Leu Pro Glu Arg Pro Ser
        210                 215                 220

Leu Tyr Thr Lys Val Val His Tyr Arg Lys Trp Ile Lys Asp Thr Ile
225                 230                 235                 240

Val Ala Asn Pro
```